(12) United States Patent
Levy et al.

(10) Patent No.: US 7,074,990 B2
(45) Date of Patent: Jul. 11, 2006

(54) CAROTENOIDS RICH PAPRIKA CULTIVARS

(75) Inventors: Arieh Levy, Rehovot (IL); Ezra Menagem, Rehovot (IL); Joseph Kanner, Rehovot (IL); Michal Barzilai, Rehovot (IL)

(73) Assignee: Agricultural Research Organization, The Volcani Center, Beit-Dagan (IL)

( * ) Notice: Subject to any disclaimer, the term of this patent is extended or adjusted under 35 U.S.C. 154(b) by 177 days.

(21) Appl. No.: 10/607,103

(22) Filed: Jun. 27, 2003

(65) Prior Publication Data

US 2004/0268448 A1 Dec. 30, 2004

(51) Int. Cl.
*A01H 5/00* (2006.01)
*A01H 1/00* (2006.01)
*A01H 5/10* (2006.01)
*A01H 4/00* (2006.01)
*C12N 5/04* (2006.01)

(52) U.S. Cl. .................. 800/317.1; 800/260; 800/295; 435/410

(58) Field of Classification Search ................ 800/260, 800/263, 264, 266, 268, 269, 317, 317.1
See application file for complete search history.

(56) References Cited

U.S. PATENT DOCUMENTS

| 2,412,707 | A | 12/1946 | Barnett |
| 2,917,539 | A | 12/1959 | Isler et al. |
| 3,206,316 | A | 9/1965 | Kläui |
| 4,400,398 | A | 8/1983 | Coenen et al. |
| 4,680,314 | A | 7/1987 | Nonomura |
| 5,079,016 | A | 1/1992 | Tood, Jr. |
| 5,310,554 | A | 5/1994 | Haigh |
| 5,382,714 | A | 1/1995 | Khachik |
| 5,648,564 | A | 7/1997 | Ausich et al. |
| 5,705,180 | A | 1/1998 | Schlipalius |
| 5,962,756 | A | 10/1999 | Koch et al. |
| 6,200,597 | B1 | 3/2001 | Mehta et al. |
| 6,380,442 | B1 | 4/2002 | Madhavi et al. |
| 6,428,816 | B1 | 8/2002 | Schlipalius et al. |
| 2004/0268448 | A1 | 12/2004 | Levy et al. |

FOREIGN PATENT DOCUMENTS

EP 0242148 1/1993

OTHER PUBLICATIONS

Mendez et al. 2000. J. Agric. Food Chem. 48: 3857-3864.*
Levy et al. 1995. J. Agric. Food Chem. 43: 362-366.*
Govindarajan "Capsicum—Production, Technology, Chemistry, and Quality. Part III. Chemistry of the Color, Aroma, and Pungency Stimuli", CRC Critical Reviews in Food Science and Nutrition, 24(3): 245-355, 1986.
Ittah et al. "Hydrolysis Study of Carotenoid Pigments of Paprika (Capsicum Annuum L. Variety Lehava) by HPLC/Photodiode Array Detection", Journal of Agricultural and Food Chemistry, 41: 889-901, 1993.
Mínguez-Mosquera et al. "Color Quality in Paprika", Journal of Agricultural and Food Chemistry, 40: 2384-2388, 1992.
Almela et al. "Carotenoid Composition of New Cultivars of Red Pepper for Paprika", Journal of Agricultural and Food Chemistry, 43: 362-366, 1991.

* cited by examiner

*Primary Examiner*—David H. Kruse
*Assistant Examiner*—Keith O. Robinson

(57) ABSTRACT

Paprika cultivars being characterized by fruits having total carotenoids content higher than 10 mg/g dry fruit weight and a branching pattern suitable for mechanical harvesting and methods and systems generating same.

15 Claims, No Drawings

CAROTENOIDS RICH PAPRIKA CULTIVARS

FIELD AND BACKGROUND OF THE INVENTION

The present invention relates to cultivars of paprika rich in carotenoids and, more particularly, to carotenoids rich cultivars of *Capsicum annuum* which produce high fruit yields and are adapted to mechanical harvest.

Paprika cultivars are used commercially to produce powders, oleoresins and concentrates as food colorants. These products are typically very rich in carotenoids. Carotenoids are isoprenoid compounds, with an extensive conjugated double bond system. They are divided into two main classes; carotenes [acyclic (lycopene) and cyclic (beta.-carotene)], and xanthophylls (e.g., capsanthin)]. In contrast to carotenes, which are pure polyene hydrocarbons, xanthophylls also contain hydroxy, epoxy and keto groups. The carotenoids form a group of pigments which have a yellow or red color and confer the characteristic colors on many food and cosmetic stuffs. Epidemiological studies have moreover shown that frequent and regular consumption of carotenoids reduces the risk of chronic disorders, including cardiovascular disorders, and has a beneficial effect on cancer prevention. This protective function of the carotenoids is seen both in their action as antioxidants and, as in the case of beta-carotene, in their provitamin A activity [see Journal of the American Dietetic Association, 97: 991–996 (1997)]. In particular, the mixture of these three carotenoids represents a system with particular antioxidant properties. Accordingly, carotenoids are highly sought for due to their nutritive and medicinal values.

Paprika carotenoids include beta-carotene, zeaxanthin, lutein, capsanthin, capsorubin and cryptocapsin, which confer substantial nutritional and medical values. Epidemiological studies have shown that frequent and regular consumption of catotenoids, such as paprika carotenoids, reduces risks of chronic disorders, such as cardiovascular disorders (Kohlmeier L et al. 1995. Am. J. Clin. Nutr. 62: 137–146) or cancer (Murakoshi et al., 1992. Cancer Res. 52: 6583–6587; Levy et al. 1995. Nutr. Cancer 24: 257–267; and Tanaka et al., 1994. Carcinogenesis 15: 15–19).

The total carotenoids content in most known commercial paprika cultivars varies from 2 to 8 milligram per gram dry fruit weight (Govindarajan, 1986. Crit. Rev. Food Sci. Nutr. 24:245–355; and Mingez-Mosquera et al. 1992. J. Agric. Food Chem. 40:2384–2388). In comparison, rich carotenoids tomato cultivars contain less than 0.15 milligram carotenoids per gram dry fruit weight. These substantial differences in carotenoids content emphasizes the high value the paprika crop as a preferred source for carotenoids being used by nutritional, nutraceutical, and pharmaceutical industries.

While reducing the present invention to practice, the present inventors have generated new cultivars of paprika which are characterized by being highly rich in carotenoids. In addition, these cultivars produce high fruit yields and are adapted to mechanical harvest. Thus, the paprika cultivars of this invention represent a valuable commercial source for nutritive and/or medicinal carotenoids, as well as to carotenoids used in the dye industry.

SUMMARY OF THE INVENTION

According to one aspect of the present invention there is provided a paprika plant, or its parts, which is being characterized by fruits having total carotenoids content higher than 10 mg/g dry fruit weight and a branching pattern suitable for mechanical harvesting.

According to another aspect of the present invention there is provided a seed of the paprika plant of the present invention.

According to yet another aspect of the present invention there is provided a tissue culture of regenerable cells of the paprika plant of the present invention.

According to still another aspect of the present invention there is provided a method of generating a paprika plant having a high carotenoids content using plant breeding techniques which employ a paprika plant, or its parts, as a source of plant breeding material, the method comprising utilizing paprika plants *Capsicum annuum* cv. Lehava and *Capsicum annuum* line 4126 as a source of breeding material.

According to an additional aspect of the present invention there is provided a method of generating a paprika plant using plant breeding techniques which employ a paprika plant, or its parts, as a source of plant breeding material, the method comprising utilizing paprika plant *Capsicum annuum* cv. 1056, (ATCC Accession No: PTA-5147) or *Capsicum annuum* cv. 1057 (ATCC Accession No: PTA-5148) as a source of breeding material.

According to still an additional aspect of the present invention there is provided a system for developing a paprika plant having a high carotenoids content using plant breeding techniques, the system comprising paprika plants *Capsicum annuum* cv. Lehava, and *Capsicum annuum* line 4126, or parts of the paprika plants, as a source of the breeding material.

According to yet an additional aspect of the present invention there is provided a system for developing a paprika plant using plant breeding techniques, the system comprising paprika plant *Capsicum annuum* cv. 1056, (ATCC Accession No: PTA-5147) or *Capsicum annuum* cv. 1057 (ATCC Accession No: PTA-5148) as a source of breeding material.

According to further features in preferred embodiments of the invention described below, the fruit of the paprika plant of the present invention is characterized by a beta carotene content higher than 1.5 mg/g dry fruit weight.

According to still further features in the described preferred embodiments the of the invention described below, the branching pattern of the paprika plant of the present invention is characterized by a branching angle not exceeding 40 degrees from main stem and branching points which occurs at a height of at least 30 cm above ground in mature plants.

According to still further features in the described preferred embodiments of the invention described below, the paprika plant of the present invention is further characterized by having an average height exceeding the average height of a *Capsicum annuum* cv. Lehava plant being of a similar age and grown under similar conditions.

According to still further features in the described preferred embodiments of the invention described below, the paprika plant of the present invention is further characterized by having a number of fruits per plant exceeding the number of fruits per plant of a *Capsicum annuum* cv. Lehava plant being of a similar age and grown under similar: conditions.

According to still further features in the described preferred embodiments of the invention described below, the paprika plant of the present invention is further characterized by having a dry fruit yield exceeding the dry fruit yield of a *Capsicum annuum* cv. Lehava plant being of a similar age and grown under similar conditions.

According to still further features in the described preferred embodiments of the invention described below, the paprika plant of the present invention is *Capsicum annuum* cv. 1056, representative seeds thereof having been deposited under ATCC Accession No: PTA-5147.

According to still further features in the described preferred embodiments of the invention described below, the paprika plant of the present invention is *Capsicum annuum* cv. 1057, representative seeds thereof having been deposited under ATCC Accession No: PTA-5148.

According to still further features in the described preferred embodiments of the invention described below the paprika plant of the present invention is further characterized at maturity by at least one trait selected from the group consisting of plant height exceeding 90 cm, an average fruit length of at least 11 cm, an average fruit width of at least 2.9 cm, an average fruit dry weight of at least 3.5 g, an average number of fruits per plant of at least 11.7 fruits and an average fruit dry weight yield of at least 0.65 kg per $m^2$.

According to still further features in the described preferred embodiments of the invention described below the paprika plant of the present invention is further characterized at maturity by having light brown seeds.

According to still further features in the described preferred embodiments of the invention described below the paprika plant of the present invention is further characterized at maturity by having light yellow seeds.

According to still further features in the described preferred embodiments of the invention described below, the tissue culture of regenerable cells of the paprika plant of the present invention is capable of expressing all the morphological and physiological characteristics of the paprika plant.

According to still further features in the described preferred embodiments of the invention described below, the tissue culture of regenerable cells of the paprika plant of the present invention Is regenerated from cells or protoplasts of a tissue selected from the group consisting of seeds, leaves, stems pollens, roots, root tips, anthers, ovules, petals, flowers, embryos, fibers and bolls.

According to still further features in the described preferred embodiments of the invention described below, the method of generating a paprika plant having high carotenoids content is effected by using plant breeding techniques which are selected from the group consisting of recurrent selection, backcrossing, pedigree breeding, restriction fragment length polymorphism enhanced selection, genetic marker enhanced selection, and transformation.

The present invention successfully addresses the shortcomings of the presently known configurations by providing carotenoids rich paprika cultivars which produce high fruit yields and are amenable to mechanical harvest and methods and systems generating same.

DESCRIPTION OF THE PREFERRED EMBODIMENTS

The present invention is of paprika (*Capsicum annuum*) cultivars which are characterized primarily by exceptionally high carotenoids content and which are also characterized by high fruit yields and morphological suitability for mechanical harvesting.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Terminology

As used herein the term "line" refers to the genetic complement contained in the plant.

As used herein the phrase "breeding line" refers to a homozygous plant line which can be used to breed a specific cultivar.

As used herein the phrase "homozygous plant" refers to a plant in which both sets of chromosomes contain essentially identical alleles in all locations.

As used herein the term "cultivar" refers to a plant of a specific line which results from a selective breeding and maintained by cultivation, and with characteristics that make it unique, such as morphological characteristics or content of specific molecules (e.g., carotenoids).

As used herein the phrase "full maturity" refers to a growth stage wherein fruits are dark red in color and exhibit loss of turgor.

Paprika is an important and valuable field crop. Thus, a primary goal of paprika breeding is to select and develop plants that have the traits that result in superior varieties.

As is illustrated in the Examples section which follows, the present inventors have generated paprika plant breeding lines which are characterized by a combination of traits which makes such plants highly suitable for use as a source of carotenoids for the food, drug and dye industries.

Thus, according to one aspect of this invention there is provided a paprika plant which is characterized by fruit having total carotenoids content higher than 10 mg/g dry fruit weight (dfw) and a branching pattern and fruits suitable for mechanical harvesting. A branching pattern suitable for mechanical harvesting is typically characterized by branching which starts at least 30 cm above ground and at an angle not exceeding 40 degrees from the main stem. Plants exhibiting such branching patterns create compact non-profuse foliage which is compatible to the limited capacity of a standard paprika harvester; moreover, the fruits should be easily detachable from stems.

As is further illustrated in Example 3 of the Examples section which follows, analysis of the fruit of the paprika plant of the present invention, revealed that total carotenoids content and beta carotene content are substantially higher than that of standard commercial paprika cultivars. The paprika plants of the present invention exhibited total carotenoids content that is at least 60% higher than that of known commercial cultivars. In addition, the paprika plants of the present invention exhibited extremely high beta carotene content (higher than 1.5 mg/g dfw) which translates into at least 200% increase of this specific carotenoid over commercial paprika cultivars.

As is mentioned hereinabove and as is illustrated in Example 2 of the Examples section which follows, the paprika plants of the present invention are also highly amenable to mechanical harvest further substantiating the commercial applicability of these cultivars. Accordingly, the mature plants compactly branch at a height of at least 30 cm above ground and at an angle not exceeding 40 degrees from the main stem. In addition, mature fruits are easily separated from plants. Therefore, the paprika plants of the present invention can be harvested mechanically and thus are suitable for large scale cultivation.

Thus, the paprika plants of the present invention are highly suitable as a source of carotenoids. Techniques for extracting and processing carotenoids from plants are described, for example, in U.S. Pat. Nos. 2,412,707; 2,917,539; 3,206,316; 4,400,398; 4,680,314; 5,382,714; 5,648,564; 5,310,554; 5,962,756; and 6,380,442; and European Patent Application No. 0 242,148.

Extracted carotenoids can be utilized for nutraceutical or pharmaceutical purposes. For example, carotenoids have been used as a source for vitamin A (retinol) production and have been implicated for use as cancer preventative agents [for example, Bollag, 1979. Cancer Chemother. Pharmacol. 3:207–215; Sporn et al., 1981, In: Zedeck et al., (eds), Inhibition of Tumor Induction and Development, pp.71–100, Plenium Publishing Corp., New York; Bertram et al., In: M. S. Arnot et al., 1982 (eds.), Molecular Interactions of Nutrition and Cancer, pp. 315–335, Raven Press, New York; and U.S. Pat. Nos. 5,705,180; 6,200,597, and 6,428,816]. In addition, various forms of natural carotenoids have been used for at least a century as food and/or feed additives in human or animal diet and/or as food and cosmetic natural colorants, such as for example, colorants for margarine and butter. Recently, color stabilized carotenoid colorants have been disclosed (U.S. Pat. No. 5,079,016).

The paprika plant of the present invention is exemplified by cultivars 1056 and 1057, representative seed thereof having been deposited under ATCC Accession Nos: PTA-5147 and PTA-5148, respectively.

These cultivars were generated from crossing the commercial cultivar "Lehava" and the breeding line 4126, as described in Example 1 of the Examples section that follows. Briefly, the breeding line 4126 was originated from a spontaneous mutant, which contained high carotenoids content, but had a low yielding potential and was unsuitable for mechanical harvesting. The two lines, 4126 and Lehava, were crossed, self pollinated and selected over six successive generations. Subsequently two homozygous lines were selected and designated as cultivars 1056 and 1057. These new cultivars were grown in the field to maturity under standard agronomic practices and evaluated comparatively with the commercial cultivar (Lehava) for their morphological and chemical characteristics The paprika plants of the present invention also have additional morphological and physiological characteristics including a higher height, higher number of fruits per plant and a higher fruit yield, as compared with the standard commercial cultivar Lehava.

The paprika cultivars described herein can be used to generate additional cultivars which exhibit the characteristics of the paprika plant of the present invention. Plants resultant from crossing any of these cultivars with another plant can be utilized in pedigree breeding, transformation and/or backcrossing to generate additional cultivars which exhibit the characteristics of the paprika plants of the present invention and any other desired traits. Screening techniques employing molecular or biochemical procedures well known in the art can be used to ensure that the important commercial characteristics sought after are preserved in each breeding generation.

The goal of backcrossing is to alter or substitute a single trait or characteristic in a recurrent parental line. To accomplish this, a single gene of the recurrent parental line is substituted or supplemented with the desired gene from the nonrecurrent line, while retaining essentially all of the rest of the desired genes, and therefore the desired physiological and morphological constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered or added to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred. Likewise, transgenes can be introduced into the plant using any of a variety of established transformation methods well-known to persons skilled in the art, such as: Gressel., 1985. Biotechnologically Conferring Herbicide Resistance in Crops: The Present Realities, In: Molecular Form and Function of the plant Genome, L van Vloten-Doting, (ed.), Plenum Press, New York; Huftner, S. L., et al., 1992, Revising Oversight of Genetically Modified Plants, Bio/Technology; Klee, H., et al., 1989, Plant Gene Vectors and Genetic Transformation: Plant Transformation Systems Based on the use of Agrobacterium tumefaciens, Cell Culture and Somatic Cell Genetics of Plants; and Koncz, C., et al. 1986, Molecular and General Genetics.

A comparison of paprika cultivars 1056 and 1057 to their parental lines (see, Examples section), demonstrates that these paprika plants exhibit several economically and agronomically advantageous traits over its respective parental lines. In particular the combination of high total carotenoids content, in particular high beta carotene content, and growth pattern suitable for mechanical harvesting, distinct the paprika plants of the present invention from prior art commercial cultivars.

Once established, the paprika plants of the present invention can be propagated from seeds or alternatively by using tissue culturing techniques.

As used herein the phrase "tissue culture" refers to plant cells or plant parts from which paprika plants can be generated, including plant protoplasts, plant cali, plant clumps, and plant cells that are intact in plants, or part of plants, such as seeds, leaves, stems, pollens, roots, root tips, anthers, ovules, petals, flowers, embryos, fibers and bolls.

Techniques of generating plant tissue culture and regenerating plants from tissue culture are well known in the art. For example, such techniques are set forth by Vasil., 1984. Cell Culture and Somatic Cell Genetics of Plants, Vol I, II, III, Laboratory Procedures and Their Applications, Academic Press, New York; Green et al., 1987. Plant Tissue and Cell Culture, Academic Press, New York; Weissbach and Weissbach. 1989. Methods for Plant Molecular Biology, Academic Press; Gelvin et al., 1990, Plant Molecular Biology Manual, Kluwer Academic Publishers; Evans et al., 1983, Handbook of Plant Cell Culture, MacMillian Publishing Company, New York; and Klee et al., 1987. Ann. Rev. of Plant Phys. 38:467–486.

The tissue culture can be generated from cells or protoplasts of a tissue selected from the group consisting of seeds, leaves, stems, pollens, roots, root tips, anthers, ovules, petals, flowers, embryos, fibers and bolls.

It will be appreciated that the plant lines of the present invention can also be used in plant breeding along with other paprika plants in order to generate novel plant lines which exhibit at least some of the characteristics of the paprika plants of the present invention.

For example, *Capsicum annuum* cv. 1056 or 1057 can be sexually crossed with other known paprika cultivars and the resulting progeny screened for plants having desirable characteristics.

Thus, the present invention provides novel paprika Cultivars, and seeds and tissue culture for generating same. This aspect of the present invention further provides a system and method for developing such paprika plants.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Generation of Paprika Cultivars 1056 and 1057

Cultivars breeding: The paprika cultivars, cv.1056 and cv. 1057, were derived from a cross between *Capsicum annuum* cv. Lehava, which is the leading commercial paprika cultivar in Israel, and a spontaneous *Capsicum annuum* mutant having an exceptionally high carotenoids content and distinctively dark red pods at maturity and dark seeds. Following three cycles of controlled self-fertilization of the mutant, a homozygous inbred line was obtained, denoted 4126 (Levy et al. 1995. Carotenoids pigments and beta carotenes in paprika fruits (*Capsicum* spp.) with different genotypes. J. Agric. Food. Chem. 43:362–366]. The 4126 line was characterized by exceptionally high carotenoids content (16.6 mg/g fruit dry weight). However, the 4126 line was also characterized by having a relatively low fruit yield, and a relatively strong attachment of fruit to the stem, as compared with the commercial cultivar Lehava, making it unsuitable for mechanical harvest.

Thus, a breeding program was carried, aimed at combining the desired traits of high carotenoids content from line 4126 with the high yield and suitability to mechanical harvest from cultivar Lehava. Accordingly, the cultivar Lehava and line 4126 were crossed (F1), then self-fertilized and selected, using a pedigree breeding method, over the F2–F6 generations. This breeding program resulted in the development of homozygous lines which retained the desired traits. Subsequently, two cultivars were selected from these lines and were designated as *Capsicum annuum* cv. 1056 and *Capsicum annuum* cv. 1057.

Example 2

Morphological Characterization of Cultivars 1056 and 1057

Field evaluation procedure: The morphological and chemical characteristics of the novel cultivars 1056 and 1057 were evaluated comparatively with the standard commercial cultivar Lehava.

Three randomized field plots, each 7.68 $m^2$ in size, were used as replicates. Seeds of the three cultivars were sown in the spring in three rows, 50 cm apart on 1.92 m wide soil beds. Following emergence, the seedlings were thinned to a density of 6–7 seedlings per meter. The plots were irrigated with cumulative amount of 750 $m^3$ of water and were fertilized with 23 and 7.5 kg of nitrogen and potassium, respectively, per 1000$m^2$.

Immediately following harvest, the plants were measured for height, fruit size, number and fruit weight. In addition, fruits were chemically analyzed for their carotenoids content.

Results: Plants of both cultivars 1056 and 1057 were taller than those of the Lehava cultivar (by 44.0% and 25.3%, respectively) and had a compact non-profuse branching indistinguishable from the Lehava cultivar, and therefore were found to be highly suitable for mechanical harvesting. Cultivar 1056 had light brown seeds, while cultivars 1057 and Lehava had light yellow and ivory color, respectively. Further characterization (summarized in Table 1 below), showed that the average fruit length, width and dry weight values of cultivars 1056 and 1057 were similar or slightly lower than that of the Lehava cultivar. On the other hand, the number of fruits per plant of cultivars 1056 and 1057 was higher than that of the Lehava cultivar, resulting in a substantially higher fruit dry yields per plant (by 31.0 and 43.1% respectively).

TABLE 1

Morphological characteristics of the plant and fruit of cultivars 1056 and 1057 in comparison with the commercial cultivar Lehava

| Cultivar | Plant height (cm) | Fruit (cm) length | Fruit (cm) width | Ratio length/width | Fruit dry weight(g) | Fruit dry yield kg/$m^2$ | No. Fruits per plant |
|---|---|---|---|---|---|---|---|
| Lehava | 78.2 (3.0)* | 13.4 (1.0) | 3.8 (0.2) | 3.5 (0.1) | 4.9 (0.6) | 0.58 (0.17) | 11.4 (2.1) |
| cv. 1056 | 112.6 (6.5) | 12.0 (1.0) | 3.4 (0.2) | 3.5 (0.4) | 3.8 (0.3) | 0.76 (0.11) | 15.6 (3.3) |
| cv. 1057 | 98.0 (7.3) | 13.3 (1.0) | 3.1 (0.2) | 4.3 (0.4) | 3.9 (0.4) | 0.83 (0.10) | 14.3 (2.6) |

*Values are means of three replicates, in parenthesis, standard errors of the means.

Example 3

Chemical Characterization of Cultivars 1056 and 1057 Separation and Quantification of Carotenoids from Paprika Varieties Paprika fruits of the cultivars described herein were harvested at full ripe maturation, i.e., when fruits turned red and exhibited loss of turgor. The fruit pericarp was dehydrated by freeze-drying and ground by a coffee grinder to a fine powder. The powder was stored in closed bottles at −20° C. until used for chemical extraction and analysis.

The content of total carotenoids was determined by dissolving a 25 mg sample of paprika powder in 25 ml of acetone for 18 hours at room temperature in the dark. The extract solution was then analyzed for the carotenoids pigment-color intensity of at 474 nm by a spectrophotometer (HP 8452A). The total carotenoids density was then estimated based on capsanthin extension coefficient of 1% = 1905 A.

The content of separated carotenoids was analyzed using the procedure described by Y. Ittah et al., 1993. (Hydrolysis study of carotenoids pigments of paprika by HPLC/photodiode array detection J. Agric. Food. Chem. 41: 889–901). Briefly, paprika powder (30 mg) was suspended in a 2% BHT (butylated hydroxy toluene) solution in 7.5 ml of absolute ethanol, followed by adding 1.25 ml of a 60% KOH aqueous solution. The suspension was then stirred under nitrogen at 37° C. for 30 min and immediately thereafter chilled on ice for 10 min. Water (5 ml) was then added to the extract followed by repeated additions of 5 mg hexane aliquots, until no color could be observed in the extract. The combined hexane extract was then dried over anhydrous sodium sulfate and evaporated under nitrogen and the dried extract was added to 1 ml of acetone (HPLC grade), passed through a 0.2 μm filter and injected into a high-performance liquid chromatography (HPLC) column (LiChrospher® 100 reversed phase C18 column, 250/4 mm; particle size −5 μm) connected to, a photodiode array detector (SPD-M10Avp) and a software system which controlled all the equipment and carried out data integration and processing (CLASS-VP, Shimadzu). HPLC conditions were as follows: a flow rate of 1 mL/min, an injection volume of 10 μl; elution was effected using the solvent gradient of Table 2 (below), detection was at 474 nm.

TABLE 2

| Elution gradient | | |
|---|---|---|
| % water | % acetone | Time, min |
| 25 | 75 | 10 |
| 25 | 75 | 5 |
| 5 | 95 | 5 |
| 5 | 95 | 7 |
| 0 | 100 | 5 |
| 25 | 75 | 5 |

(M. Isabel M'ingiez-Mosquera and D'amaso Horero-M'endez. Separation and quantification of the Carotenoid Pigments in Red Peppers, Paprika, and Oleoresin by Reversed-Phase HPLC. J. Agri. Food. Chem. 1993, 41, 1616–20.)

Following HPLC separation, the densities of specific carotenoids in sample extracts were estimated using the integrated area of the compound peaks and calculated from the total carotenoids. The ASTA value of each sample was determined by multiplying the optical density value of 1 mg paprika powder in 1 ml acetone solution by 164.

As summarized in Table 3 below, the content of total carotenoids of cultivars 1056 and 1057 was 134 and 124.4 mg/10g dry fruit weight (dfw, respectively). Compared with total carotenoids content of 77.6 mg/10g dfw characterizing the Lehava cultivar, the cultivars of the present invention exhibited a 72.7% (1056) and 60.3% (1057) increase in total carotenoids content. Furthermore, the beta-carotene content of cultivars 1056 and 1057, was 17.6 and 18.4 mg/10g dfw, respectively, compared with just 5.5 mg/10g dfw found in the Lehava cultivar, which translates to a 220% and 234.5% increase, respectively. The total carotenoids content and the beta carotene content of cultivars 1056 and 1057 are among the highest reported in paprika fruits (Govindarajan, 1986. Crit. Rev. Food Sci. Nutr. 24:245–355; and Mingez-Mosquera et al. 1992. J. Agric. Food Chem. 40:2384–2388).

TABLE 3

Chemical characteristics of the fruits of cultivars 1056 and 1057 in comparison with the commercial cultivar Lehava.

| Cultivar | Total carotenoids mg/10 g.d.w. | ASTA Units | Beta-carotene mg/10 g.d.w. | Capsanthin mg/10 g.d.w. | Vitamin E mg/10 g.d.w. |
|---|---|---|---|---|---|
| Lehava | 77.6 (1.8) | 233.1 (13.4) | 5.5 (0.1) | 28.0 (1.6) | 3.4 (0.1) |
| cv. 1056 | 134.0 (9.2) | 402.5 (28.3) | 17.6 (1.6) | 41.7 (2.0) | 3.9 (0.1) |
| cv. 1057 | 124.4 (3.8) | 373.6 (11.4) | 18.4 (0.4) | 36.5 (1.3) | 3.0 (0.1) |

*d.w. = dry weight
**values are means of three replication, in parenthesis the standard errors of the means.

Thus, paprika cultivars 1056 and 1057 exhibited substantially higher contents of total carotenoids and of beta carotene, as compared to existing commercial cultivars (Almela et al., 1991. J. Agric. Food Chem. 39:1606–1609; Levi el al., 1995. J. Agric. Food Chem. 43:362–366). In addition these two new cultivars were found to be high yielding and suitable for mechanical harvesting. Therefore, cultivars 1056 and 1057 are superior to existing commercial paprika cultivars, particularly as a source of nutritional and/or medicinal carotenoids.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition citation or identification of any reference in this application shall not be construed as an admission that such reference is available as prior art to the present invention.

Seed Deposit

Propagating material of the paprika plant cultivars of the present invention is maintained by American Type Culture Collection (Manassas, Va. 201 10) since Apr. 22, 2003 under the following depository numbers: PTA-5147 and PTA-5148. Access to this deposit will be available during the pendency of this application to persons determined by the Commissioner of Patents and Trademarks to be entitled thereto under 37 CFR 1.14 and 35 USC 122. Upon allowance of any claims in this application, all restrictions on the availability to the public of the variety will be irrevocably removed by affording access to a deposit of at least 2500 seeds of germplasm of these varieties.

What is claimed is:

1. A paprika plant, or a part thereof, the paprika plant being characterized by fruits having a total carotenoids content higher than 10 mg/g dry fruit weight and a branching pattern suitable for mechanical harvesting, wherein the paprika plant is *Capsicum annuum* cv. 1056 or 1057, representative seeds thereof having been deposited under ATCC Accession Nos: PTA-5147 or PTA-5148, respectively.

2. The paprika plant of claim 1, wherein said fruit of the paprika plant is characterized by a beta carotene content higher than 1.5 mg/g dry fruit weight.

3. The paprika plant of claim 1, wherein said branching pattern is characterized by a branching angle not exceeding 40 degrees from main stem and branch points which occurs at a height of at least 30 cm above ground in mature plants.

4. The paprika plant of claim 1, further characterized by having an average height exceeding the average height of a *Capsicum annuum* cv. Lehava plant being of a similar age and grown under similar conditions.

5. The paprika plant of claim 1, further characterized by having a number of fruits per plant exceeding the number of fruits per plant of a *Capsicum annuum* cv. Lehava plant being of a similar age and grown under similar conditions.

6. The paprika plant of claim 1, further characterized by having a dry fruit yield exceeding the dry fruit yield of a *Capsicum annuum* cv. Lehava plant being of a similar age and grown under similar conditions.

7. A seed of the paprika plant of claim 1.

8. A tissue culture of regenerable cells produced from the paprika plant of claim 1.

9. The tissue culture of claim 8, wherein the tissue culture regenerates plants having all the morphological and physiological characteristics of the paprika plant. *Capsicum annuum* cv. 1056 or 1057, representative seeds thereof having been deposited under ATCC Accession Nos: PTA-5147 or PTA-5148, respectively.

10. The tissue culture of claim 8, wherein the tissue culture is produced from cells or protoplasts of a tissue selected from the group consisting of seeds, leaves, stems, pollens, roots, root tips, anthers, ovules, petals, flowers and embryos.

11. The paprika plant of claim 1, wherein the paprika plant is further characterized at maturity by at least one trait selected from the group consisting of plant height exceeding 90 cm, an average fruit length of at least 11 cm, an average fruit width of at least 2.9 cm, an average fruit dry weight of at least 3.5 g, an average number of fruits per plant of at least 11.7 fruits and an average fruit dry weight yield of at least 0.65 kg per m$^2$.

12. The paprika plant of claim 11, wherein the paprika plant is further characterized at maturity by having brown seeds.

13. The paprika plant of claim 11, wherein the paprika plant is further characterized at maturity by having light yellow seeds.

14. A method of generating a paprika plant comprising crossing paprika plant *Capsicum annuum* cv. 1056, (ATCC Accession No: PTA-5147) or *Capsicum annuum* cv. 1057 (ATCC Accession No: PTA-5148) with another paprika plant.

15. The method of claim 14, wherein a plant breeding technique is used in generating the paprika plant, the plant breeding technique is selected from the group consisting of recurrent selection, backcrossing, pedigree breeding, restriction fragment length polymorphism enhanced selection and genetic marker enhanced selection.

* * * * *